(12) United States Patent
Takacs et al.

(10) Patent No.: US 9,514,380 B2
(45) Date of Patent: Dec. 6, 2016

(54) METHOD FOR IMAGE PROCESSING AND AN APPARATUS

(71) Applicants: Nokia Corporation, Espoo (FI); The Board of Trustees of the Leland Stanford Junior University, Palo Alto, CA (US)

(72) Inventors: Gabriel Takacs, Santa Clara, CA (US); Radek Grzeszczuk, Menlo Park, CA (US); David Chen, Mountain View, CA (US); Shang-Hsuan Tsai, Stanford, CA (US); Vijay Chandrasekhar, Stanford, CA (US); Bernd Girod, Stanford, CA (US)

(73) Assignees: Nokia Corporation, Espoo (FI); The Board of Trustees of the Leland Stanford Junior University, Palo Alto, CA (US)

( * ) Notice: Subject to any disclaimer, the term of this patent is extended or adjusted under 35 U.S.C. 154(b) by 77 days.

(21) Appl. No.: 13/682,498

(22) Filed: Nov. 20, 2012

(65) Prior Publication Data

US 2013/0129223 A1 May 23, 2013

Related U.S. Application Data

(60) Provisional application No. 61/562,346, filed on Nov. 21, 2011.

(51) Int. Cl.
*G06K 9/46* (2006.01)
*G06K 9/66* (2006.01)
(Continued)

(52) U.S. Cl.
CPC ............. *G06K 9/46* (2013.01); *A61B 3/032* (2013.01); *G06F 17/30247* (2013.01);
(Continued)

(58) Field of Classification Search
CPC . G06F 17/30247; G06K 9/209; G06K 9/4671; H04N 19/463; H04N 19/91; H04N 19/59
(Continued)

(56) References Cited

U.S. PATENT DOCUMENTS

2005/0058359 A1* 3/2005 Tashman ............ G06K 9/00664
382/243
2006/0239591 A1* 10/2006 Kim .................. G06F 17/30038
382/305
(Continued)

OTHER PUBLICATIONS

Extended European Search Report from European Patent Application No. 12850757.1 dated Mar. 9, 2015.
(Continued)

*Primary Examiner* — Gregory M Desire
(74) *Attorney, Agent, or Firm* — Alston & Bird LLP

(57) ABSTRACT

The disclosure relates to a method in which one or more local descriptors relating to an interest point of an image are received. A global descriptor is determined for the image on the basis of the one or more local descriptors; and the global descriptor is compressed. The disclosure also relates to an apparatus comprising a processor and a memory including computer program code, and storage medium having stored thereon a computer executable program code for use by an apparatus.

30 Claims, 13 Drawing Sheets

(51) Int. Cl.
*A61B 3/032* (2006.01)
*G06F 17/30* (2006.01)
*H04N 19/463* (2014.01)
*H04N 19/91* (2014.01)
*H04N 19/80* (2014.01)
*H04N 19/85* (2014.01)
*H04N 19/59* (2014.01)

(52) U.S. Cl.
CPC ......... *G06K 9/4671* (2013.01); *H04N 19/463* (2014.11); *H04N 19/59* (2014.11); *H04N 19/80* (2014.11); *H04N 19/85* (2014.11); *H04N 19/91* (2014.11)

(58) Field of Classification Search
USPC .......................................................... 382/195
See application file for complete search history.

(56) References Cited

U.S. PATENT DOCUMENTS

| | | | |
|---|---|---|---|
| 2010/0246969 | A1 | 9/2010 | Winder et al. |
| 2010/0310174 | A1 | 12/2010 | Reznik |
| 2011/0081090 | A1 | 4/2011 | Bouguet et al. |
| 2012/0076401 | A1* | 3/2012 | Sanchez et al. ............ 382/159 |
| 2012/0121192 | A1* | 5/2012 | Kim et al. .................. 382/201 |
| 2013/0279762 | A1* | 10/2013 | Pau ...................... G06T 7/2033 382/107 |

OTHER PUBLICATIONS

Chen, David et al.; "Residual Enhanced Visual Vectors for On-Device Image Matching"; *Signals, Systems and Computers (Asilomar), 2011 Conference Record of the Forty Fifth Asilomer Conference on, IEEE*; Nov. 6, 2011; pp. 850-854; XP032172217.
Girod, Bernd et al.; "Mobile Visual Search"; *IEEE Signal Processing Magazine*; vol. 28, No. 4; Jul. 1, 2011; pp. 61-76; XP011367629.
Takacs, Gabriel et al.; "Unified Real-Time Tracking and Recognition with Rotation-Invariant Fast Features"; *2010 IEEE Conference on Computer Vision and Pattern Recognition (CVPR)*; Jun. 13-18, 2010; Jun. 13, 2010; pp. 934-941; XP031725941.
Chandrasekhar, Vijay et al.; "Compressing a Set of CHoG Features"; *Application of Digital Image Processing XXXIV*; vol. 8135, No. 1; Sep. 12, 2010; pp. 1-12; XP060021123.
Tsai S et al.; "Rate-Efficient, Real-Time CD Cover Recognition on a Camera-Phone"; *ACM Multimedia, Proceedings of the International Conference (MM '08)*, Vancouver, British Columbia, Canada, *ACM Press*; Oct. 26, 2008; pp. 1023-1024; XP002677213.
International Search Report and Written Opinion for International Application No. PCT/FI2012/051136 dated Mar. 25, 2013.
Jegou H. et al.; "Affregating Local Descriptors Into a Compact Image Representation"; *IEEE Conference on Computer Vision and Pattern Recognition*; Jun. 13, 2010, San Francisco, USA; pp. 3304-3311; XP031725868.
Chandrasekhar V. et al.; Compressed Histogram of Gradients: A Low-Bitrate Descriptor; International Journal of Computer Vision; [Online] vol. 96, Feb. 2012; pp. 384-399; XP035008617 Retrieved from the Internet: [retrieved on May 15, 2011].

\* cited by examiner

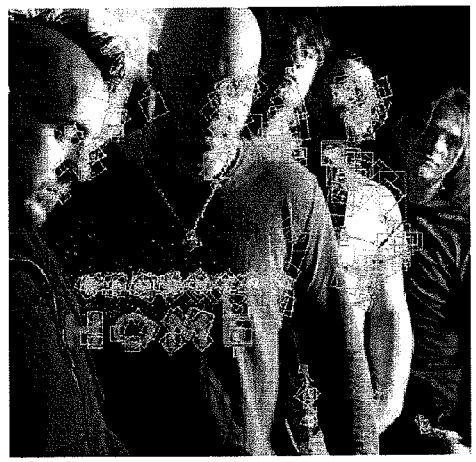 
Fig. 7a                Fig. 7b
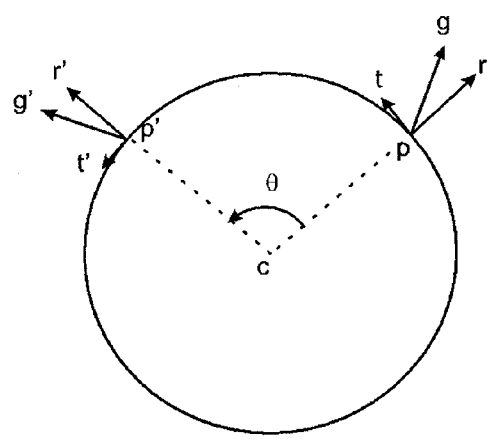
Fig. 8

- Visual Word
- Feature Descriptor
- Word Residual

METHOD FOR IMAGE PROCESSING AND AN APPARATUS

CROSS REFERENCE TO RELATED APPLICATION

This application is a nonprovisional of and claims priority to U.S. provisional application No. 61/562,346, filed Nov. 21, 2011, the entire contents of which are hereby incorporated by reference.

TECHNICAL FIELD

There is provided a method for content recognition and retrieval, an apparatus, and computer program products.

BACKGROUND INFORMATION

This section is intended to provide a background or context to the invention that is recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Image content recognition and retrieval from a database may be a desired property in certain situations. For example, a mobile device can be used to take pictures of products, objects, buildings, etc. and then the content of the image may be determined. Possibly, pictures with similar content may be searched from a database. To do this, some content recognition is performed.

This may also be applicable other devises as well, such as set-top-boxes and other computing devices.

For any object in an image there may be many features, interesting points on the object. These interesting points can be extracted to provide a feature description of the object which may be used when attempting to locate the object in an image possibly containing many other objects. For image feature generation some approaches take an image and transforms it into a large collection of local feature vectors. Each of these feature vectors may be invariant to scaling, rotation or translation of the image.

Image content description is used in a wide range of applications, including hand-held product recognition, museum guides, pedestrian navigation, set top-box video content detection, web-scale image search, and augmented reality. Many such applications are constrained by the computational power of their platforms. Even in unconstrained cases, such as web-scale image search, processing millions of images can lead to a computational bottleneck. Therefore, algorithms with low computational complexity are always desirable. Augmented reality applications may further be constrained because resources of mobile devices are shared between camera pose tracking and image content recognition. These two tasks may usually be decoupled from each other. Technologies that are fast enough for real-time tracking may not perform well at recognition from large-scale databases. Conversely, algorithms which perform well at recognition may not be fast enough for real-time tracking on mobile devices.

In addition to compatibility, a compact descriptor for visual search algorithm should be small and efficient to compute in hardware or software. Smaller descriptors may more efficiently use memory and storage, and may be faster to transmit over a network and retrieving from a database. Low-complexity descriptors may enable applications on low-power mobile devices, as well as extending the capabilities of large-scale database processing.

Mobile augmented reality systems overlay virtual content on a live video stream of real-world content. These systems rely on content recognition and tracking to generate this overlay.

To perform well on large scale retrieval tasks, interest points (aka features) that can be localized in both location and scale may be helpful. Interest points such as corners, edges etc. can be searched from an image using different algorithms such as Accelerated Segment Test. One image can include a huge number of interest points depending on the contents of the image. Some images may include dozens of interest points whereas some other images may include hundreds of or even thousands of interest points. Moreover, images can be scaled to provide different scales of the image. Then, interesting point detectors may use pixels from different scales to determine whether there exists an interest point near a current pixel.

Though Features from Accelerated Segment Test (FAST) corners can be detected at different scales, they are inherently insensitive to scale changes. Also, replicating them at many scales may create an excessively large database and unwanted redundancy. Conversely, blob detectors such as Laplacian of Gaussian (LoG), Difference of Gaussians (DoG), Determinant of Hessian (DoH), and Difference of Boxes (DoB) are all sensitive to scale variation and can thus be localized in scale space.

SUMMARY

The present invention introduces a method for providing compact descriptors for visual search. In the present invention local image features are extracted and a global image signature is formed from these local descriptors. Global features may be much smaller than local features. The local signatures are compressed using the embedded form that may be best suited for the target bit rate. The location meta-data of the local descriptors can also be compressed by using location coding. In some embodiments a complete query is formed by starting with the global signature and filling the rest of the target rate with the compressed local descriptors. This method may provide good performance at a wide range of bit rates, and may maintain compatibility between queries of different rates. In other words, the global descriptor is included and the rest of the possibly available budget is filled with local descriptors.

Multi-scale difference of boxes (DoB) filters can be used to find blobs in an image scale-space. In some embodiments each level of the scale space is subsampled to its critical anti-aliased frequency. This provides the data with minimal processing. Furthermore, the results of the filters are re-used to produce an image scale-space which may be required for later feature description. Radial gradients may also be computed at each interest point and placed them into precomputed, oriented spatial bins.

According to a first aspect of the present invention there is provided a method comprising:
  receiving one or more local descriptors relating to an interest point of an image;
  compressing the descriptors; and
  determining a global descriptor for the image on the basis of the one or more local descriptors.

According to a second aspect of the present invention there is provided an apparatus comprising a processor and a memory including computer program code, the memory and the computer program code configured to, with the processor, cause the apparatus to:

receive one or more local descriptors relating to an interest point of an image;
compress the global descriptors; and
determine a global descriptor for the image on the basis of the one or more local descriptors.

According to a third aspect of the present invention there is provided a storage medium having stored thereon a computer executable program code for use by an apparatus, said program code comprises instructions for:

receiving one or more local descriptors relating to an interest point of an image;
compressing the descriptors; and
determining a global descriptor for the image on the basis of the one or more local descriptors.

According to a fourth aspect of the present invention there is provided an apparatus comprising:

means for receiving one or more local descriptors relating to an interest point of an image;
means for compressing the descriptors; and
means for determining a global descriptor for the image on the basis of the one or more local descriptors.

The present invention provides an interest point detector which has relatively low complexity. The descriptor computation re-uses the results of interest point detection. The interest point detector may provide a properly antialiased and subsampled scale-space at no additional cost. Further, no pixel interpolation or gradient rotation is needed. This is possible because radial gradients enable to place the gradient, without any modification, in a proper spatial bin.

The rotation invariant fast feature descriptor according to the present invention can be sufficiently fast to compute and track in real-time on a mobile device, and sufficiently robust for large-scale image recognition.

One advantage of this tracking scheme is that the same rotation invariant fast feature descriptors can be matched against a database for image recognition without the need for a separate descriptor pipeline. This may reduce the query latency, leading to a more responsive user experience. In some embodiments the basic rotation invariant fast feature descriptor can be extended to one that uses polar spatial binning and a permutation distance, wherein the accuracy may further be increased.

DESCRIPTION OF THE DRAWINGS

For better understanding of the present invention, reference will now be made by way of example to the accompanying drawings in which:

FIG. 7a illustrates an example of interest point detection for an intra-scale mode;

FIG. 7b illustrates an example of interest point detection for an inter-scale mode;

FIG. 8 illustrates examples of radial gradients;

DETAILED DESCRIPTION

Figure 1:
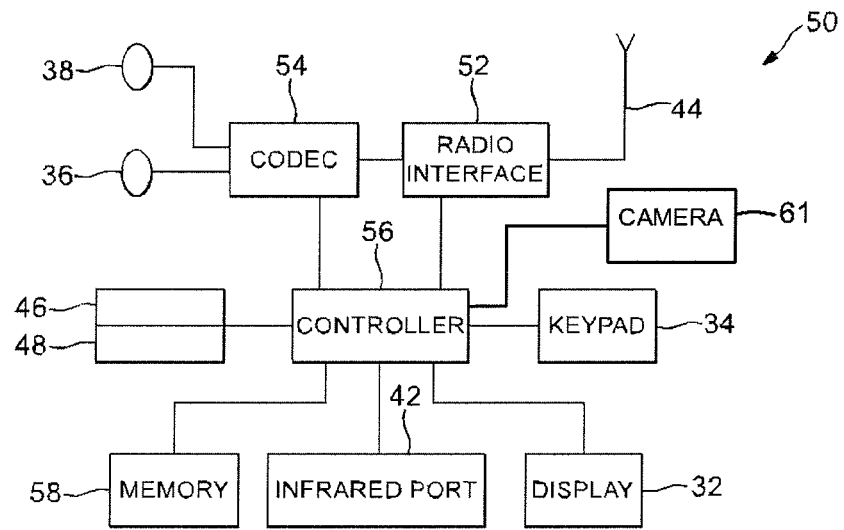
FIG. 1 shows schematically an electronic device employing some embodiments of the invention.
Figure 2:
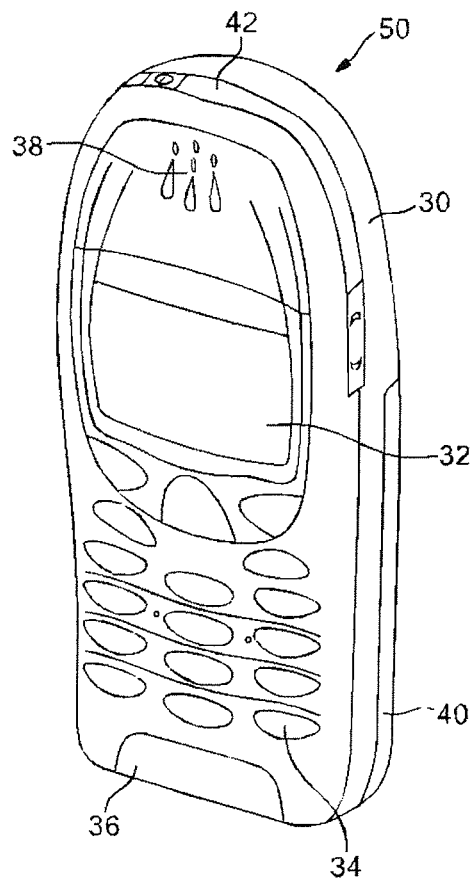
FIG. 2 shows schematically a user equipment suitable for employing some embodiments of the invention.

The following describes in further detail suitable apparatus and possible mechanisms for the provision of improving the image content recognition and retrieval from a database. In this regard reference is first made to FIG. 1 which shows a schematic block diagram of an exemplary apparatus or electronic device 50, which may incorporate an apparatus according to an embodiment of the invention.

The electronic device 50 may for example be a mobile terminal or user equipment of a wireless communication system. However, it would be appreciated that embodiments of the invention may be implemented within any electronic device or apparatus which may require image content recognition and/or retrieval.

The apparatus 50 may comprise a housing 30 for incorporating and protecting the device. The apparatus 50 further may comprise a display 32 in the form of a liquid crystal display. In other embodiments of the invention the display may be any suitable display technology suitable to display an image or video. The apparatus 50 may further comprise a keypad 34. In other embodiments of the invention any suitable data or user interface mechanism may be employed. For example the user interface may be implemented as a virtual keyboard or data entry system as part of a touch-sensitive display. The apparatus may comprise a microphone 36 or any suitable audio input which may be a digital or analogue signal input. The apparatus 50 may further comprise an audio output device which in embodiments of the invention may be any one of: an earpiece 38, speaker, or an analogue audio or digital audio output connection. The apparatus 50 may also comprise a battery 40 (or in other embodiments of the invention the device may be powered by any suitable mobile energy device such as solar cell, fuel cell or clockwork generator). The apparatus may further comprise an infrared port 42 for short range line of sight communication to other devices. In other embodiments the apparatus 50 may further comprise any suitable short range communication solution such as for example a Bluetooth wireless connection or a USB/firewire wired connection.

The apparatus 50 may comprise a controller 56 or processor for controlling the apparatus 50. The controller 56 may be connected to memory 58 which in embodiments of the invention may store both data in the form of image and audio data and/or may also store instructions for implementation on the controller 56. The controller 56 may further be connected to codec circuitry 54 suitable for carrying out coding and decoding of audio and/or video data or assisting in coding and decoding possibly carried out by the controller 56.

The apparatus 50 may further comprise a card reader 48 and a smart card 46, for example a UICC and UICC reader for providing user information and being suitable for providing authentication information for authentication and authorization of the user at a network.

The apparatus 50 may comprise radio interface circuitry 52 connected to the controller and suitable for generating wireless communication signals for example for communication with a cellular communications network, a wireless communications system or a wireless local area network. The apparatus 50 may further comprise an antenna 44 connected to the radio interface circuitry 52 for transmitting radio frequency signals generated at the radio interface circuitry 52 to other apparatus(es) and for receiving radio frequency signals from other apparatus(es).

In some embodiments of the invention, the apparatus 50 comprises a camera 61 capable of recording or detecting individual frames which are then passed to the codec 54 or controller for processing. In some embodiments of the invention, the apparatus may receive the image data for processing from another device prior to transmission and/or storage. In some embodiments of the invention, the apparatus 50 may receive either wirelessly or by a wired connection the image for processing.

Figure 3:
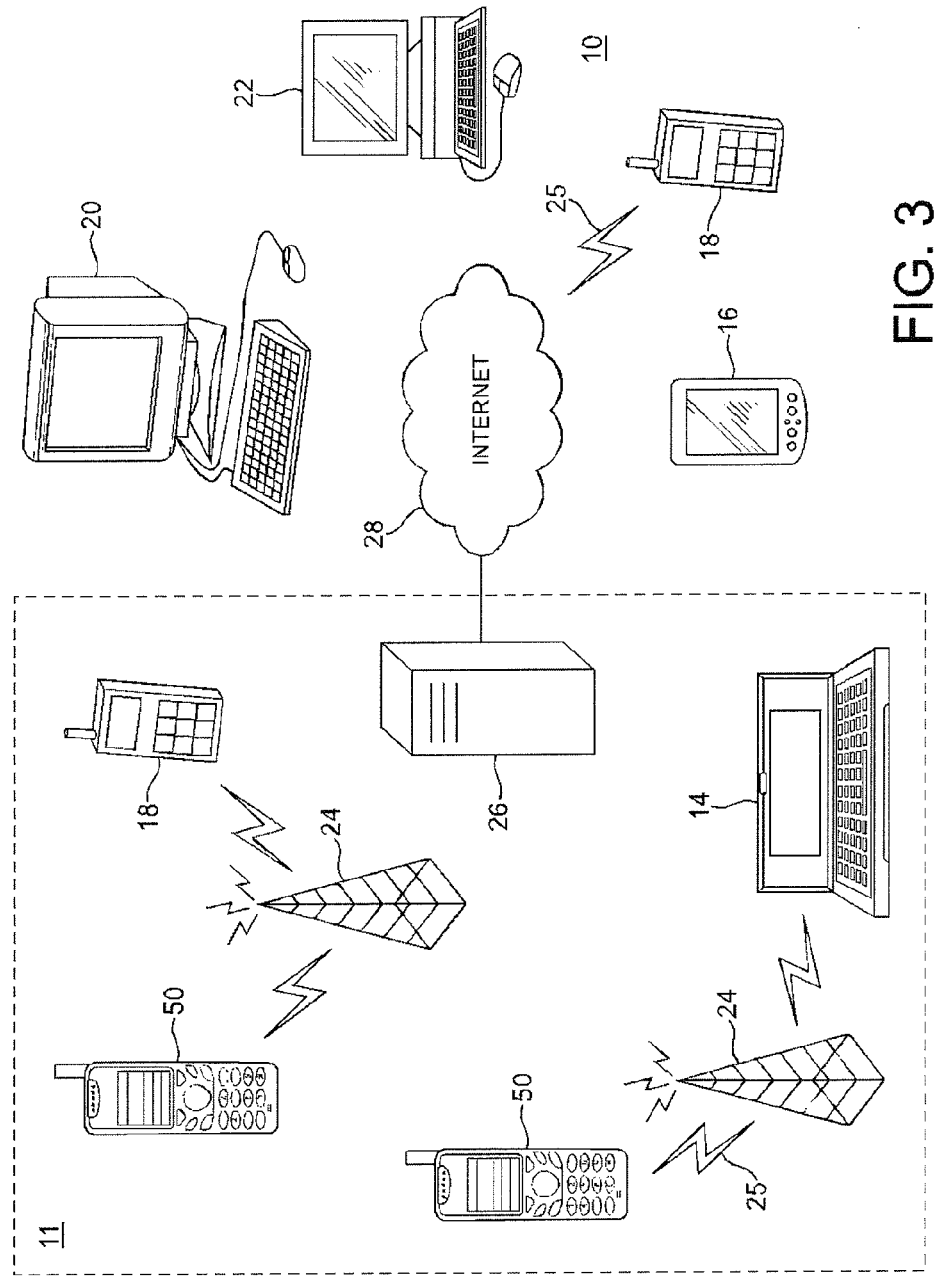
FIG. 3 further shows schematically electronic devices employing embodiments of the invention connected using wireless and wired network connections.

With respect to FIG. 3, an example of a system within which embodiments of the present invention can be utilized is shown. The system 10 comprises multiple communication devices which can communicate through one or more networks. The system 10 may comprise any combination of wired or wireless networks including, but not limited to a wireless cellular telephone network (such as a GSM, UMTS, CDMA network etc), a wireless local area network (WLAN) such as defined by any of the IEEE 802.x standards, a Bluetooth personal area network, an Ethernet local area network, a token ring local area network, a wide area network, and the Internet.

The system 10 may include both wired and wireless communication devices or apparatus 50 suitable for implementing embodiments of the invention.

For example, the system shown in FIG. 3 shows a mobile telephone network 11 and a representation of the internet 28. Connectivity to the internet 28 may include, but is not limited to, long range wireless connections, short range wireless connections, and various wired connections including, but not limited to, telephone lines, cable lines, power lines, and similar communication pathways.

The example communication devices shown in the system 10 may include, but are not limited to, an electronic device or apparatus 50, a combination of a personal digital assistant (PDA) and a mobile telephone 14, a PDA 16, an integrated messaging device (IMD) 18, a desktop computer 20, a notebook computer 22. The apparatus 50 may be stationary or mobile when carried by an individual who is moving. The apparatus 50 may also be located in a mode of transport including, but not limited to, a car, a truck, a taxi, a bus, a train, a boat, an airplane, a bicycle, a motorcycle or any similar suitable mode of transport.

Some or further apparatuses may send and receive calls and messages and communicate with service providers through a wireless connection 25 to a base station 24. The base station 24 may be connected to a network server 26 that allows communication between the mobile telephone network 11 and the internet 28. The system may include additional communication devices and communication devices of various types.

The communication devices may communicate using various transmission technologies including, but not limited to, code division multiple access (CDMA), global systems for mobile communications (GSM), universal mobile telecommunications system (UMTS), time divisional multiple access (TDMA), frequency division multiple access (FDMA), transmission control protocol-internet protocol (TCP-IP), short messaging service (SMS), multimedia messaging service (MMS), email, instant messaging service (IMS), Bluetooth, IEEE 802.11 and any similar wireless communication technology. A communications device involved in implementing various embodiments of the present invention may communicate using various media including, but not limited to, radio, infrared, laser, cable connections, and any suitable connection.

Figure 4:
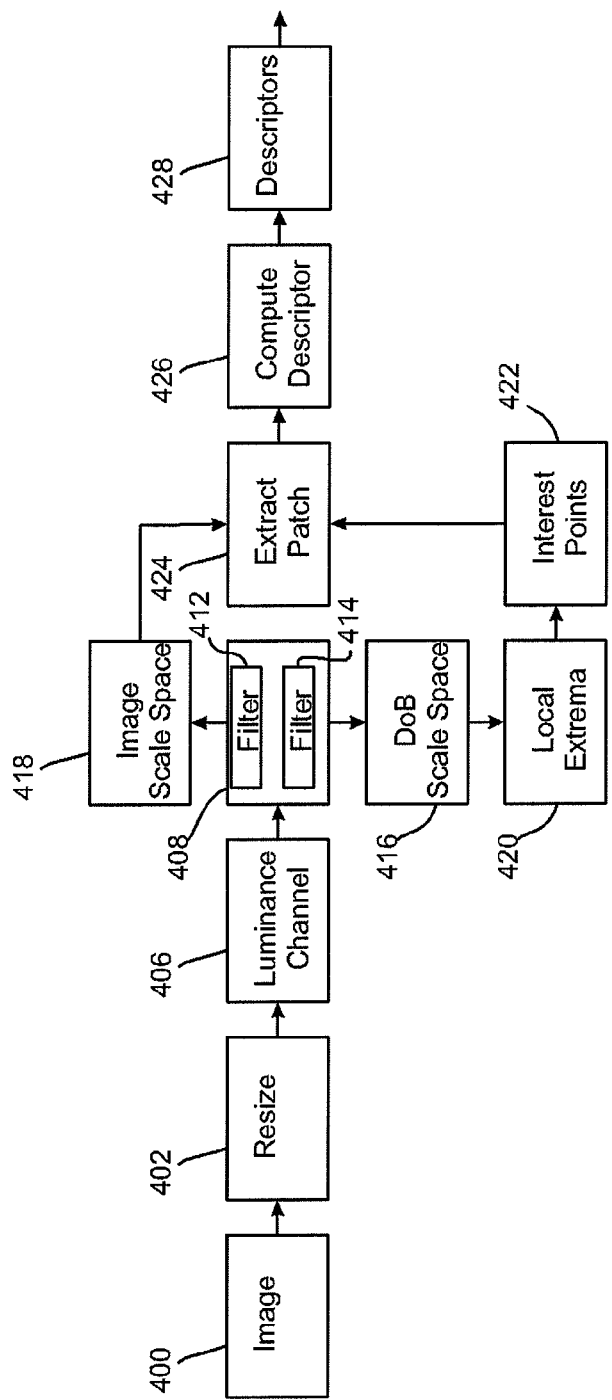
FIG. 4 shows schematically an embodiment of the invention as incorporated within an apparatus.
Figure 5:
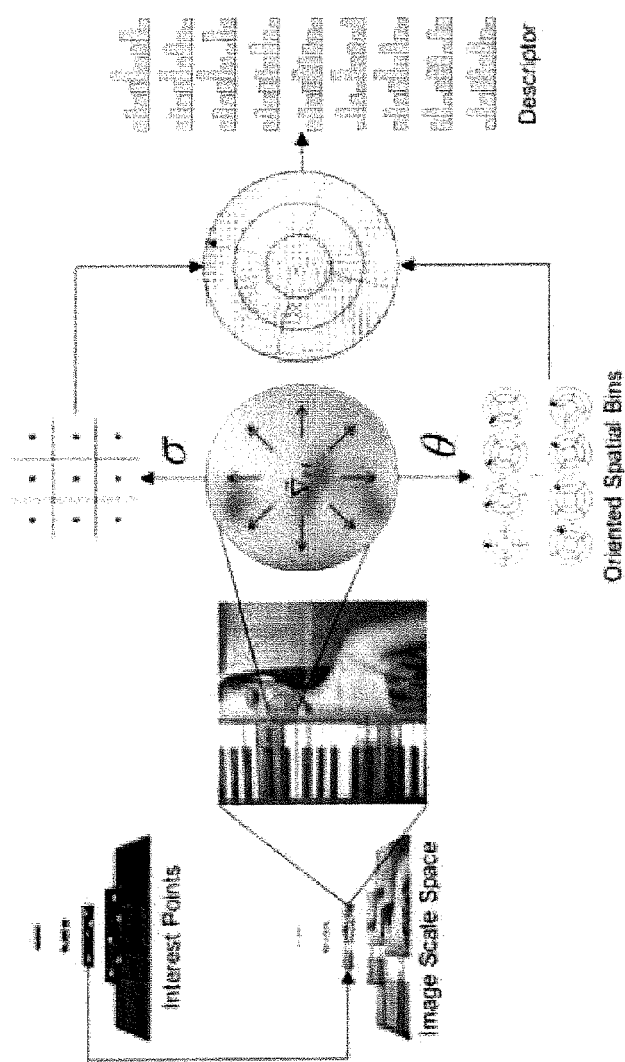
FIG. 5 shows schematically a rotation invariant fast feature descriptor pipeline according to an embodiment of the invention.
Figure 11:
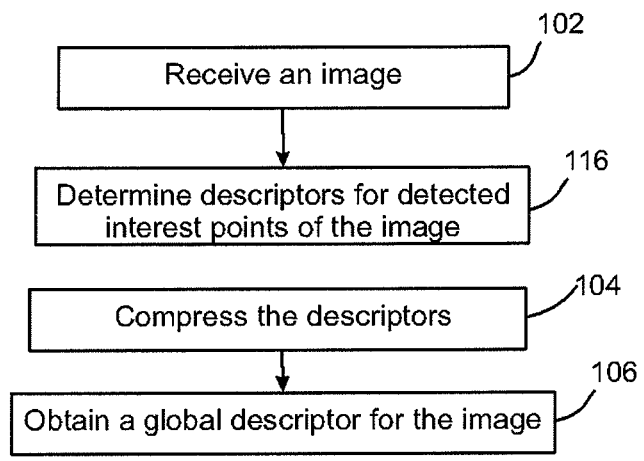
FIG. 11 is a flow diagram of showing the operation of an embodiment of the invention.

In the following the method according to an example embodiment will be disclosed in more detail with reference to the apparatus of FIG. 4 and to the flow diagram of FIG. 11. The apparatus 50 receives 102 an image 400 from an image source which may be a camera, a database, a communication network such as the internet, or another location. In some embodiments the image may have been stored to the memory 58 of the apparatus from which the controller 56 may read it for processing. The image may be a so-called snapshot image or still image, or it may be a frame of a video signal. When the image is a snapshot or still image, the apparatus 50 may use the method, for example, to search similar images from a database, from a network, etc. When the image is part of a video sequence the apparatus 50 may use the method for tracking one or more objects in the video sequence and possibly highlight the location of the object in the video sequence or display another visible indication on the basis of the location and movement of the object in the video sequence.

In some embodiment the image 400 may be resized 402 before processing. or the processing may be performed to the received image without first resizing it. In the luminance channel 406 luminance information is extracted from the image i.e. pixel values which represent brightness at the locations of the pixels in the image.

The controller 56 may have determined an area in the memory 58 for storing the image and for processing the image. The image may be read to an image memory and provided to one or more filters which form one or more filtered representations of the image into the memory 58. These representations may also be called as scales or scale levels. In some embodiments the number of different scales may be between 1 and 5 but also larger number of scales may be formed. The first scale (s=0) is the original image. The second scale (s=1), which is the first filtered version of the original image, may have half the resolution of the original image. Thus, the image of the second scale may be formed by downsampling the original image by 2. In some embodiments the downsampling is performed by including only part of the pixels of the original pixel into the downsampled image in both x and y directions. For example, the image on the second scale level may contain every other pixel of the original image, the image on the third scale level may contain every third pixel of the original image, the image on the fourth scale level may contain every fourth pixel of the original image, etc. In some other embodiments the downsampling uses two or more pixels of the original image to form one pixel of the scaled image.

In other words, an image can be represented at different resolutions by e.g. filtering the original image to form a coarser image. The coarser image can further be filtered to form a further image etc. The resolution of the images at each filtering stage may be reduced. For example, the original image is first downsampled to half of the resolution of the original image, this image is downsampled to one-third of the resolution of the original image, the next level is one-fourth of the original image etc. This kind of stack of images can also be called as an image pyramid. In other words, an image pyramid is a representation of an image at different resolutions. One type of the image pyramid is a mipmap pyramid. The mipmap pyramid is a hierarchy of filtered versions of an original image so that successive levels correspond to filtered frequencies. In other words, the mipmap pyramid decomposes an image into a series of filtered images. The mipmap pyramid can use a variety of filters, including a box filter and a Gaussian filter.

The original image and the scaled images are provided to the filter section 408 for filtering. In some embodiments, to be robust to image scale changes, filter responses are computed for a range of filter scales, yielding a stack of filtered images. Thus, F is a scalar valued function that covers a 3-dimensional scale-space. If the dimensions of I are w×h pixels, and N is the number of scales, then the scale space has dimensions w×h×N pixels. For reasonable coverage of possible scales, a range that covers ~3 octaves (up to an 8× scale change) may be chosen. In some embodiments N is chosen to be greater than or equal to 8 (N>8) and s covers all integers 1 . . . N. This is a linear covering of scale-space. This gives finer resolution at large scales than an exponential coverage. However, at small scales, the resolution is similar for both scale-space coverings.

In some embodiments box filters are used which use pixels around a selected pixel in filtering. The filter response may be a simple weighted difference of two box filters that are centered on the same point (the selected pixel) but have different scales. For a scale parameter, s, the inner box may have width 2s+1 and the outer box may be roughly twice the size with width 4s+1. The filter response is thus given by $$(2s+1)^{-2}\Sigma_{in} - (4s+1)^{-2}\Sigma_{out} \quad (1a)$$

where Σ is a sum of pixel values within the box. These sums can be efficiently computed by using an integral image.

The Equation (1a) can be generalized by defining $$F(x,y,s) = B(x,y,s) - B(x,y,2s) \quad (1b)$$

The filters may be implemented e.g. as a computer code executable by the controller 56. These filters are called as an inner-box filter 412 and an outer-box filter 414 in this application. The inner-box filter 412 gets some pixel values around the selected pixel as input and calculates the output values B(x,y,s), e.g. $(2s+1)^{-2}\Sigma_{in}$. These values are stored into an image scale space memory buffer 416 in the memory 58 for later use in descriptor computation. Similarly, the outer-box filter 414 gets some pixel values around the selected pixel as input and calculates the output values B(x,y,2s), e.g. $(4s+1)^{-2}\Sigma_{out}$. These values may also be stored into the memory 58 as well as the values F(x,y,s) resulting from the filtering. The resulting values form a scale space representation 418 of the image.

In some embodiments the sums of pixel values within a box of a certain width (e.g. 2s+1 or 4s+1) can be computed by using an integral image (II). Let I(x,y) be an input image 400, and S(x,y) be the associated integral image, then $$S(x, y) = \sum_{v=0}^{y} \sum_{u=0}^{x} I(u, v) \quad (2a)$$

and $$\sum(x, y, s) = S(x+s, y+s, s) + \\ S(x-s-1, y-s-1) - S(x+s, y-s-1) - S(x-s-1, y+s) \quad (2b)$$

With this method it is possible to compute a filter response at any scale or position from a single integral image.

The values of the scale space are examined by a local extrema detector 420 to find local maxima and minima from the values. Given the filter response, a local maxima and minima in scale-space can be found whose absolute values are above a threshold. For each of these extrema, edge responses can be eliminated by e.g. thresholding a Harris corner score within a radius of a certain number of pixels, e.g. 5s pixels. The remaining interest points can be sorted by their absolute responses.

To compute 104 a descriptor from a given location in scale-space, anti-aliased pixels values are computed at the correct scale. Instead of recomputing these values with the integral image, or via a mipmap with trilinear interpolation, the differences of boxes (DoB) filter results B(x,y,s) stored into the image scale memory buffer 416 are reused.

As was described above, a pyramid scale space is used, where each scale is downsampled by a factor that matches the filter scale. In some embodiments, the first scale is computed on the full resolution, and the subsequent scales are downsampled by factors of 2×, 3×, 4×, etc. To make pixel locations consistent between scales, subsampling can be implemented by simply skipping over the appropriate number of pixels when computing filter responses. This approach may reduce the complexity of interest point detection.

To prevent aliasing when down-sampling, the image is low-pass filtered. For this purpose, the inner box filter values from the DoB computation are used. Each pixel at scale s is thus filtered by a rectangular filter of width 2s+1. To show that this filter is appropriate for anti-aliasing, the 1D impulse response can be considered, $$h[k] = \begin{cases} (2s+1)^{-1}, & |k| \le s \\ 0 & \text{otherwise} \end{cases} \quad (3)$$

The associated frequency response, H(ω), is given by $$H(\omega) = \frac{\sin[\omega(s+1/2)]}{(2s+1)\sin(\omega/2)}$$

The first zero crossing falls at $\omega_0 = 2\pi/(\omega/2)$. To prevent aliasing while down-sampling by a factor of s, frequencies larger than the Nyquist rate of $\omega_c = \omega/s$ shall be suppressed. Because $\omega_0 < \omega_c$ the main lobe of the filter response is contained within the Nyquist rate, and aliased frequencies are suppressed by at least 10 dB.

Not only does RIFF compute fewer filter response values, but each filter response is significantly simpler to compute. A Speeded-Up Robust Features (SURF) uses an approximate determinant of Hessian, $|H| = D_{xx}D_{yy} + (\kappa D_{xy})^2$. This requires a total of 8 box filters; 2 for each of $D_{xx}$ and $D_{yy}$, and 4 for $D_{xy}$. Each box filter requires 3 additions, and 4 memory accesses. Each of $D_{xx}$ and $D_{yy}$ also require a multiplication. Assembling the filters into |H| requires another 3 multiplications, 1 addition, and a memory access to store the result. In contrast, RIFF only uses 2 box filters, each requiring 3 additions, multiplication by a weighting term, and 4 memory accesses. Assembling the filters into the DoB response requires one more addition and two memory accesses to store the filter and image scales-space and requires one third as many operations per response.

Figure 6:
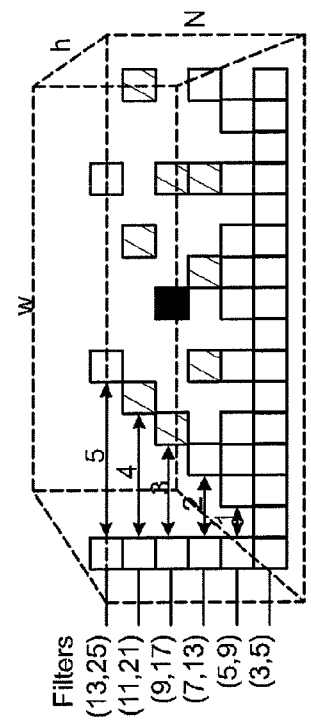
FIG. 6 illustrates an example of a sub-sampled scale-space.

FIG. 6 illustrates an example slice through the subsampled scale space. There are N scales formed from the original w×h pixel image. Pixels are subsampled according to the scale, but they are stored relative to the full scale. The shaded pixels 602 are the neighbors of the black pixel 601 which is used for inter-scale local extrema detection. Also shown are the (inner, outer) filter sizes for each scale.

The local extrema found by the local extrema detector 420 can be used to find repeatable points in scale space. However, adjacent layers of the scale space do not have the same resolution. Because of this, a simple 27-pixel 3D neighborhood is not possible, and therefore a method to compensate for the resolution change is used e.g. as follows.

The scale-space is stored in a full resolution stack of images, but only pixel values with a sampling stride equal to the scale parameter are computed as illustrated in FIG. 6. To find the neighbors of a pixel at position (x,y,s), the 8 neighbors within the same scale are first considered, given by {(x±s, y±s, s), (x, y±s, s), (x±s, y, s)}. Then the nearest existing pixels in the scales above and below are searched, (x+, y+, s+1) and (x−, y−, s−1), where $$x-=(s-1)\lfloor x/(s-1)+0.5 \rfloor \quad (4)$$

$$x+=(s+1)\lfloor x/(s+1)+0.5 \rfloor \quad (5)$$

$$y-=(s-1)\lfloor y/(s-1)+0.5 \rfloor \quad (6)$$

$$y+=(s+1)\lfloor y/(s+1)+0.5 \rfloor \quad (7)$$

Given these central pixels above and below, some neighbors (e.g. 8 neighbors) of the central pixels are searched as before. This can be called as an inter-scale detection scheme. Additionally, a point is determined to be a local extrema if it is maximal or minimal relative to some of its neighbors on the same scale, for example 8 neighbors. While the inter scheme provides full scale-space localization, the intra scheme describes points at multiple salient scales, and may be faster. FIG. 7a illustrates an example of interest point detection for an intra-scale mode and FIG. 7b illustrates an example of interest point detection 422 for an inter-scale mode. It should be noted that the interest points presented in these figures have been oriented during subsequent descriptor computation. Detected interest points are depicted as rectangles in FIGS. 7a, 7b.

Even though the DoB filter may fire strongly on blobs, it may also be sensitive to high-contrast edges. These edges may not be desirable interest points because they are poorly localized. Therefore, in some embodiments edge responses are aimed to be removed by determining whether an interest point is a corner or an edge. This may be performed e.g. by computing a Harris corner score around each detected interest point. The calculation of Harris corner scores only requires computing first derivatives. Let $D_x$ and $D_y$ be the partial derivatives in the x and y directions. The Harris matrix, H, is given by $$H = \begin{bmatrix} \langle D_x^2 \rangle & \langle D_x D_y \rangle \\ \langle D_x D_y \rangle & \langle D_y^2 \rangle \end{bmatrix} \quad (8)$$

where ⟨•⟩ represents the average over a local window of pixels. A circular window with a certain radius, such as 5s, centered on the interest point can be used. This size window is large enough to cover the box filter area while keeping computational costs low. The corner score, Mc, is then given by $$M_c = \lambda_1 \lambda_2 - \kappa(\lambda_1 + \lambda_2)^2 = \det(H) - \kappa tr(H)^2 \quad (9)$$

where the λ are eigen values of H, and κ is a sensitivity parameter. In some embodiments κ=0.1 and only interest points with a positive value of $M_c$ are kept.

Figure 12:
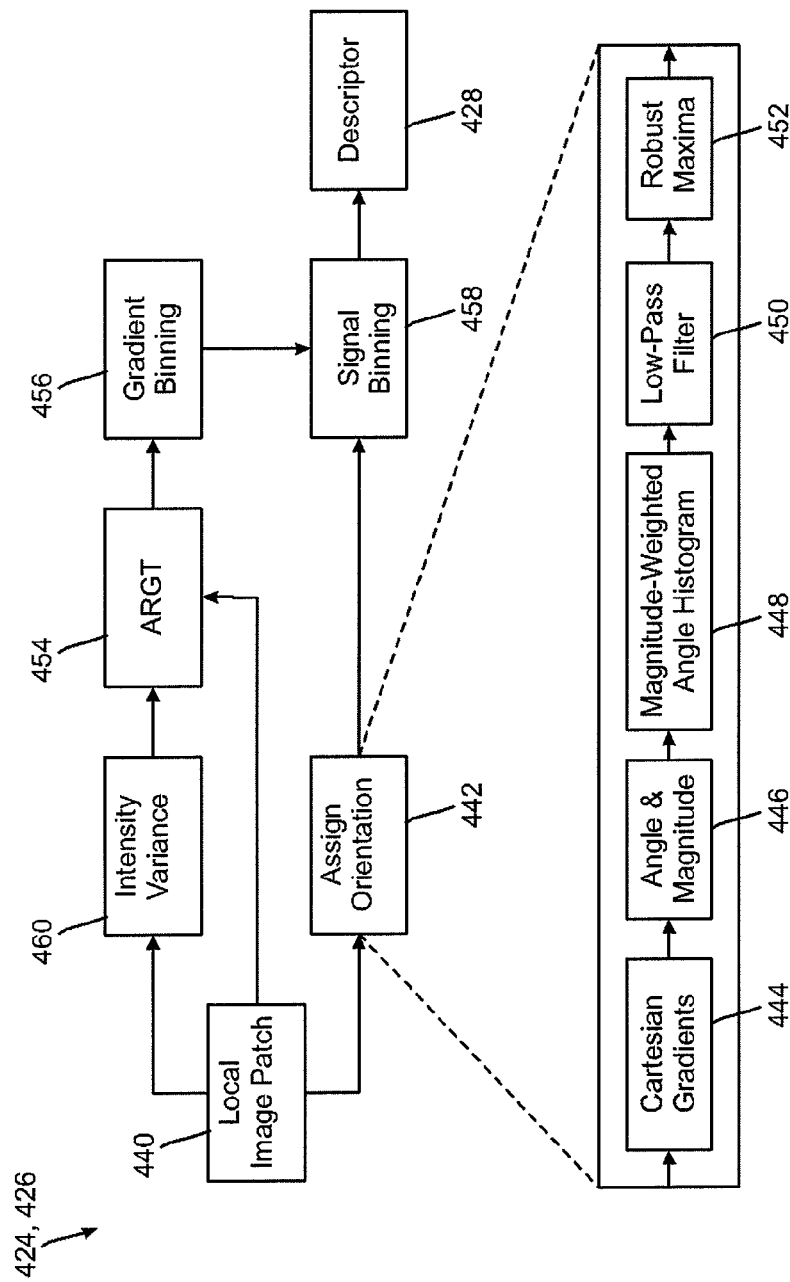
FIG. 12 shows as a block diagram an example of spatial spinning according to an embodiment of the invention as incorporated within an apparatus.

When calculating feature descriptors, some constraints may need to be taken into account. For example, during rotation, image content changes position and gradient vectors change direction. Therefore, the algorithm should be invariant to both of these changes. The interest point detector provides invariance to the change in location of image content. However, local patches around interest points may still undergo rotation to which the descriptor should be invariant. The descriptor consists of a few major components; intensity normalization, spatial binning, and gradient binning. Of these, spatial and gradient binning should be rotation-invariant. An example embodiment of the descriptor pipeline 424 is illustrated in FIG. 12. In the pipeline, patches are extracted for each descriptor and an orientation and pixel intensity standard deviation are calculated. Radial gradients are quantized and placed in spatial bins, yielding a descriptor consisting of histograms.

Given interest point locations and an image scale-space, feature descriptors can be computed by a feature descriptor computing section 424, 426. As illustrated in FIG. 12, the descriptor can be computed as follows.

A descriptor on a circular patch of a certain diameter D is computed by the extract patch section 440. The diameter D is for example 25s, centered on a point (x,y,s). The pixels in the patch are sampled with a stride of s pixels from the image scale-space 418 that was precomputed during interest point detection.

Then, orientation assignment 442 is performed. (x, y)-gradients are computed 444 for each pixel in the patch, using a [−1, 0, 1] centered difference filter and a 72-bin, magnitude-weighted histogram of the gradient orientations is formed 448. A look-up table can be used to convert pixel differences into angle and magnitude 446. With 8-bit pixel values, there are 512×512 possible gradient values. For robustness, a simple [1, 1, 1] low-pass filter 450 may be applied to the histogram. The dominant direction can be found 452 e.g. as follows. If the value of the second most dominant angle bin is within a certain threshold, such as 90% of the dominant bin's value, then the bin that is to the right of the angle that bisects the two bins is chosen. It should be noted that the patch need not be actually rotated but only the angle should be found.

FIG. 8 illustrates examples of radial gradients.

For radial gradient quantization the standard deviation, σ, of the patch is computed 460. Then, an approximate radial gradient transform (ARGT) may be computed 454. The approximate radial gradient transform should incorporate proper baseline normalization because diagonal pixel neighbors are farther than horizontal or vertical neighbors. Let b be the distance between two pixels in the approximate radial gradient transform, and q be the desired gradient quantizer step-size. The quantizer parameter, intensity and baseline normalization are combined by multiplying pixel differences by $(bq\sigma)^{-1}$. The quantized radial gradients are obtained 456 by rounding to each component to $\{-1, 0, 1\}$, yielding one of nine possible gradients.

Figure 13:
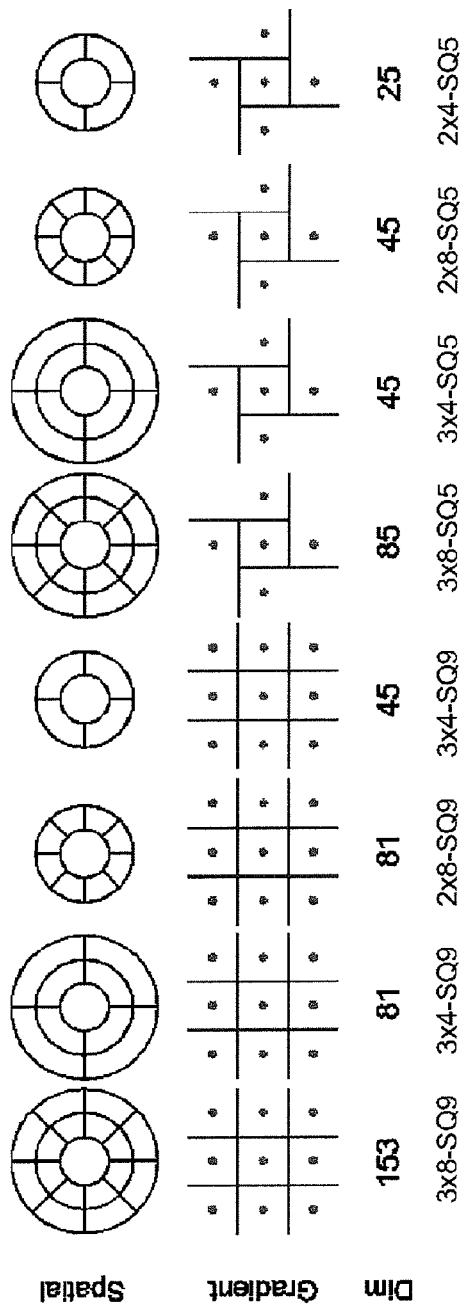
FIG. 13 illustrates an example of a set of descriptors that may be derived from a base descriptor.

Spatial spinning is depicted as block 458 in FIG. 12. Given the descriptor orientation, $\theta$, a spatial layout that is rotated by $-\theta$ is selected. For speed, the spatial bins may have been precomputed for each possible orientation. A layout with a central bin and two outer rings of 4 bins each, for a total of 9 bins, may be used as shown in FIG. 13. In each spatial bin a histogram of quantized gradients is formed which is normalized to sum to one. The resulting descriptor is 81-dimensional. The radial gradients are already rotation invariant, thus by placing them in the proper spatial bin, the entire descriptor 428 is rotation invariant.

Figure 9:
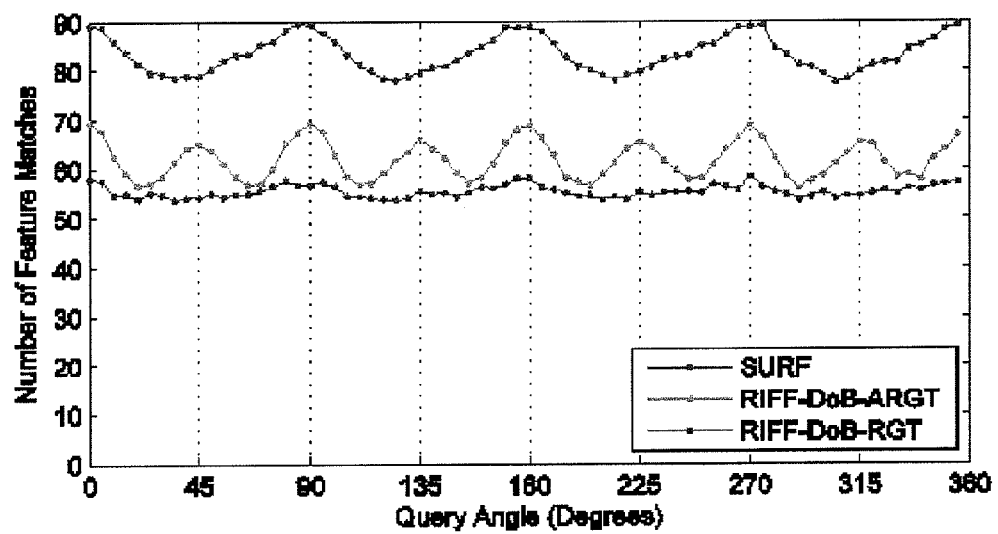
FIG. 9 illustrates the number of pairwise feature matches at different query orientations.
Figure 10:
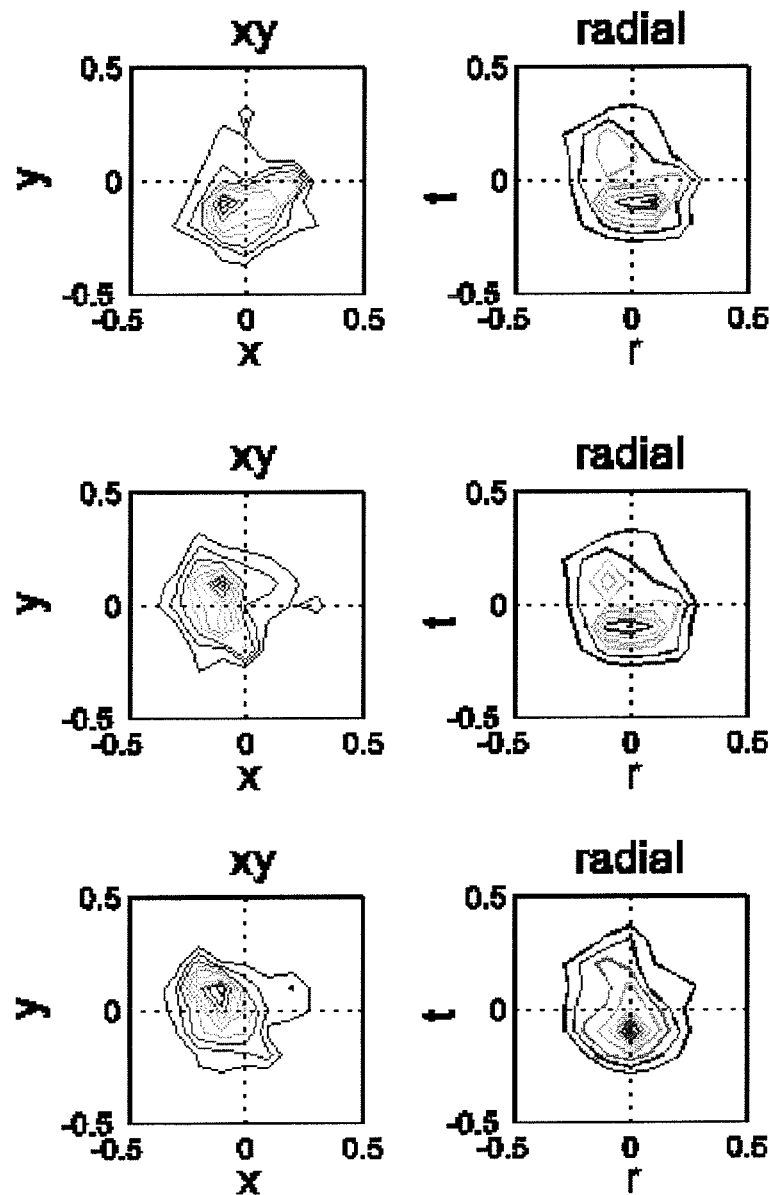
FIG. 10 illustrates a rotation invariance with the radial gradient transform.

To demonstrate that the RIFF pipeline is invariant to image rotation pairwise image matching can be used. The pairwise matching was performed on 100 pairs of images of CDs from an MPEG dataset. One of the images was rotated in 5° increments and the number of geometrically verified feature matches was recorded. To ensure that there were not edge effects, the images were cropped to circular regions and the borders were padded with 100 pixels on all sides. In FIG. 9, these results are shown for RIFF with and without approximate radial gradients, as well as for SURF. An oscillation in the SURF results with a period of 90° which is due to the anisotropy of box filters. There is a similar oscillation in the exact-RGT RIFF from the DoB filter. Using the approximate RGT introduces a higher frequency oscillation with a period of 45° which is caused by the 8-direction RGT approximation. However, this approximation generally improves matching performance.

Because the RIFF descriptor is composed of normalized histograms, some compression techniques can be applied. An entire histogram can be quantized and compressed such that the $L_1$-norm is preserved. In particular, the coding technique with a quantization parameter equal to the number of gradient bins may be used. This can yield a compressed-RIFF (C-RIFF) descriptor that can be stored in 135 bits using fixed length codes, or ~100 bits with variable length codes. This is 6.5 times less than an 8-bit per dimension, uncompressed descriptor.

In the following an example embodiment of the compression of the descriptors is discussed in more detail. The precise choice of spatial and gradient binning configurations can significantly alter the performance and size of a descriptor. However, descriptors with different configurations may not be compatible. To enable compatibility while allowing for variation in the descriptor configuration an embedded descriptor may be defined. For such a descriptor, multiple smaller descriptors may be derived from a single high-dimensional descriptor, called the base descriptor. Using this base descriptor, a subset of spatial/gradient bins can be extracted, and/or neighboring spatial/gradient bins can be combined.

FIG. 13 illustrates the set of descriptors that may be derived from the base descriptor. The configuration names are shown on below the descriptors. In this example embodiment the base descriptor uses 9 gradient bins and 17 spatial bins. The spatial bins are composed of a central disk surrounded by two rings of 8 angular bins. To reduce the number of spatial bins angular bins may be combined e.g. by averaging the distributions contained therein, and/or the outer ring may be removed. To reduce the number gradient bins neighboring bins are combined into a pin-wheel pattern e.g. by adding values of the bins to each other. Table 1 shows examples of size parameters for each embedded descriptor configuration, as well as the sizes of the descriptors. To estimate the descriptor size the entropy of the symbols produced by subsequent quantization can be measured. In some embodiments the 3x4-SQ5 configuration performs the best at and below a query size of 4096 bytes, and the 3x8-SQ9 configuration performs the best above 4096 bytes.

TABLE 1

| Name | No. Gradient Bins | No. Spatial Bins | Dimensionality | Entropy (bits) |
|---|---|---|---|---|
| 3x8-SQ9 | 9 | 17 | 153 | 206.16 |
| 2x8-SQ9 | 9 | 9 | 81 | 108.97 |
| 3x8-SQ5 | 5 | 17 | 85 | 103.06 |
| 3x4-SQ9 | 9 | 9 | 81 | 101.25 |
| 2x4-SQ9 | 9 | 5 | 45 | 55.89 |
| 2x8-SQ5 | 5 | 9 | 45 | 53.85 |
| 3x4-SQ5 | 5 | 9 | 45 | 47.07 |
| 2x4-SQ5 | 5 | 5 | 25 | 25.71 |

The gradient information is stored in each spatial bin as a distribution. This allows to apply histogram based compression techniques. For compressing 106 the descriptor, the gradient histogram is quantized in each spatial bin individually. Some quantization schemes may work well for compressing distributions: Quantization by Huffman Coding, Type Coding and optimal Lloyd-Max Vector Quantization (VQ). Here, one of the quantization schemes based on the $A_n$ lattice is briefly discussed. $A_n$ lattice is linear in complexity to the number of histogram bins and performs close to optimal Lloyd-Max VQ. Let m represent the number of histogram bins in the gradient distribution and let $P=[p_1, p_2, \ldots, p_m] \in R_+^m$ be the original distribution as described by the gradient histogram, and $Q=[q_1, q_2, \ldots, q_m] \in R_+^m$ be the quantized probability distribution. First, a lattice of distributions $Q_n=Q(k1, \ldots, km)$ with probabilities $$q_i = \frac{k}{n}, k_i, n \in Z_+, \sum_i k_i = n \tag{10}$$

is constructed.

Figure 18:
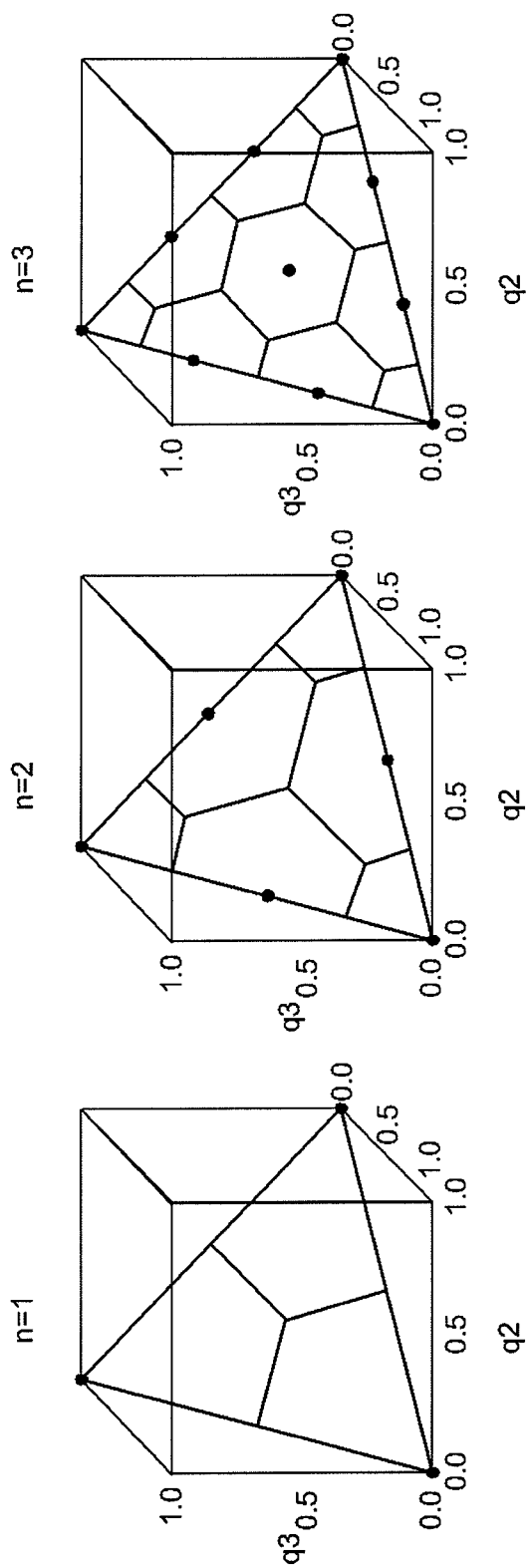
FIG. 18 depicts several example sets of quantized probability distributions in m=3 dimensions.

FIG. 18 depicts several examples of such sets in m=3 dimensions.

From the point of view of lattice theory, the set $Q_n$ is a bounded subset of an $A_n$ lattice. The parameter n controls the fidelity of quantization and the higher the value of n parameter, the higher is the fidelity. n=m provides a good trade-off between size and accuracy. Second, after quantizing the distribution P, an index for the type is computed. The total number of types K(m, n) is the number of partitions of n into m terms $k_1 + \ldots + k_m = n$ $$K(m, n) = \binom{n+m-1}{m-1} \tag{11}$$

The index may be encoded in each spatial cell with fixed-length or entropy codes. For example, a Context Adaptive Binary Arithmetic Coder (CABAC) may be used for entropy coding the symbols. The quantization scheme described here performs close to optimal Lloyd-Max VQ and does not require storage of codebooks on the mobile client.

Each interest point has a location, scale and orientation associated with it. Interest point locations are needed in the geometric verification step to validate potential candidate matches. The location of each interest point may be stored as two numbers: x and y co-ordinates in the image at sub-pixel accuracy. In a floating point representation, each feature location would require 64 bits, 32 bits each for x and y. This is comparable in size to the CHoG descriptor itself, and hence, compact representation of location data may be important.

For compressing location data, the fact that the features can be sent in any order can be exploited. Consider the sample space that represents N features. There are N! number of codes that represent the same feature set because the order does not matter. Thus, if the ordering for the feature set is fixed, i.e., using the LHC scheme described above, bit savings of log(N!) can be achieved. E.g., for a feature set of 750 features, rate savings of log(750!)/750~8 bits per feature can be achieved.

Figure 14:
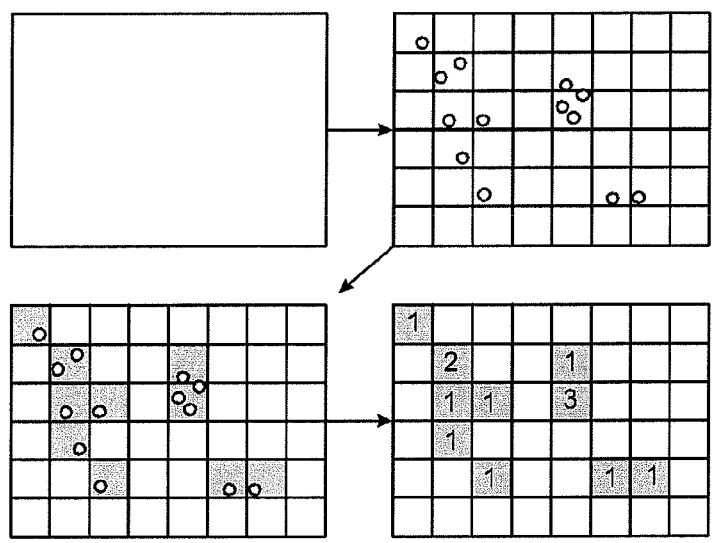
FIG. 14 depicts an example of a 2-D histogram generated from locations of descriptors

In some embodiments compression schemes based on reordering are used. The ordering gain can be obtained by reordering the descriptors, or reordering the location data associated with them. Schemes for reordering descriptors include Tree Histogram Coding, and a scheme based on Digital Search Trees. In this example the Location Histogram Coding (LHC) scheme is used as it performs well. It has been noted that the interest points in images may be spatially clustered. To encode location data, a 2-D histogram is generated from the locations of the descriptors. An example of this is depicted in FIG. 14 in which the location of the descriptors is represented using a location histogram. The image is divided into spatial bins and the number of features within each spatial bin is counted. The binary map indicating which spatial bins contains features and a sequence of feature counts, representing the number of features in occupied bins, is compressed. The binary map is encoded using a trained context-based arithmetic coder, with neighboring bins being used as the context for each spatial bin.

LHC results in a bitrate reduction of log(N!). Further, using neighboring bins as context, additional spatial correlation between the locations of different descriptors can be exploited.

It has been found that quantizing the (x,y) location to 4-pixel blocks may be sufficient for geometric verification. If a simple fixed-length coding scheme is used, then the rate will be log(640/4)+log(480/4)~14 bits/feature for a VGA size image. Using LHC, the same location data can be transmitted with ~5 bits/descriptor—a ~12.5× reduction in data compared to a 64-bit floating point representation and ~2.8× rate reduction compared to fixed-length coding. Scale and orientation data may not be included in the bitstream as they are not used in a retrieval setup.

Figure 15:
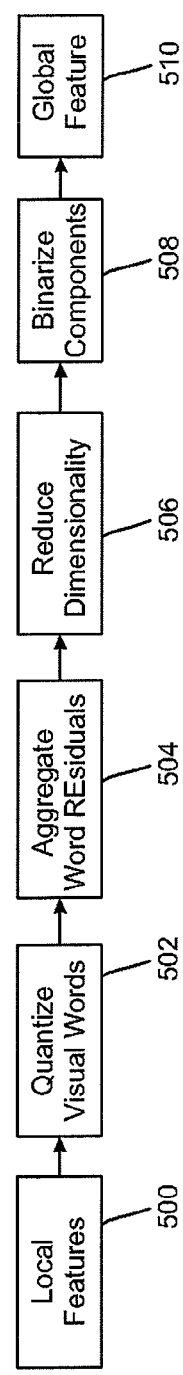
FIG. 15 illustrates an example of steps in computing a residual enhanced visual vector signature.

In addition to local features, a global descriptor 108 is also used. This global descriptor may be called as a Residual Enhanced Visual Vector (REVV). The REVV descriptor builds on a Vector of Locally Aggregated Descriptors (VLAD). As illustrated in FIG. 15, the steps in computing a REVV signature may be as follows. For quantization 502, a codebook of visual words is created offline for the local descriptors 500. The highest dimensional embedded descriptor (or the base descriptor) is used for computing the centroids. Let $c_1 \ldots c_k$ be the set of d-dimensional centroids. In a first step, each descriptor in the image is quantized to the nearest visual word. A small dictionary size k=192 may be used.

Figure 16:
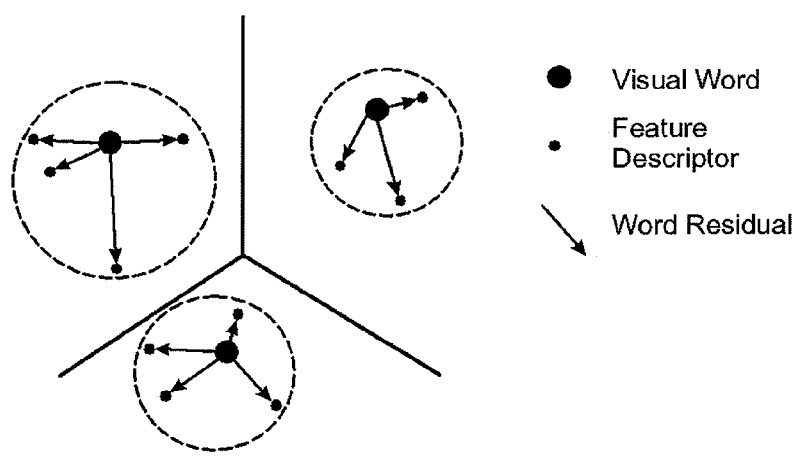
FIG. 16 illustrates an example of residual aggregation.

For aggregation 504 after quantization, a set of word residual (WR) vectors will surround each visual word, as illustrated in FIG. 16. The mean around each visual word is aggregated. A maximum of features may be defined for this step. In this example embodiment the maximum is 720. Setting a threshold on the number of features enables keeping the global signature compact. The dimensionality of the global descriptor is given by k×d, d dimensions for each centroid.

The dimensionality of the residuals is reduced 506 to a certain value dLDA, e.g. 32, using an appropriate method such as a linear discriminant analysis (LDA). With LDA, the dimensionality of the global signature can be reduced and also the performance can be boosted.

Following dimensionality reduction by LDA, each component of the transformed residual is binarized 508 to +1 or −1 depending on the sign. This signed binarization creates a compact image signature that just requires at most k×dLDA bits to represent the residuals and k bits to indicate which visual words have been visited. Fewer bits are required if some centroids are not visited by an image's features. For dLDA≤32, the binarized residual components at a visual word can be conveniently packed into a 32-bit unsigned integer. The binarization results in a compact global signature 510 of the image. Parameters can be chosen carefully that result in a global signature of ~512 bytes. The compact signature can be used for both fast indexing and retrieval at low bitrates.

One goal of the feature extraction is image recognition by matching the descriptors obtained as described above against a set of database images and to find images the descriptors of which provide accurate enough match.

With the RIFF pipeline both video tracking and content recognition can be performed by extracting features at every frame and using a tracking algorithm. For mobile augmented reality features should be extracted in real-time on a mobile device.

The present invention can be used, for example, in pairwise image matching To match a pair of images their global signatures can be compared. Because the signatures are binary, the comparison can be performed quite efficiently in the compressed domain by using the Hamming distance. If the distance is below a threshold then the pair of images may be declared as a match. However, if the distance is not below this threshold, or to localize the image content, then local feature matching may be performed.

In some example embodiments query sizes larger than 512 bytes the query contains local features and their associated locations in the image. To use these features they are first decoded to their original distributions and the descriptors are formed. The set of local features are compared using a ratio test using an approximate nearest neighbors search. This results in a set of feature matches. Using these matches and the locations of the features, an affine geometric model can be found between the two images using e.g. RANSAC. The images can be declared to match if the number of geometrically consistent feature matches is above a threshold. The resulting affine model allows to localize the image contents. It is possible that the global signature measure declares that the images match, and yet a geometrically consistent set of local feature matches may not be found. This may result at queries of small sizes, where there are very few local features. In this case the image content may be localized with a fixed rectangle in the center of the image.

Figure 17:
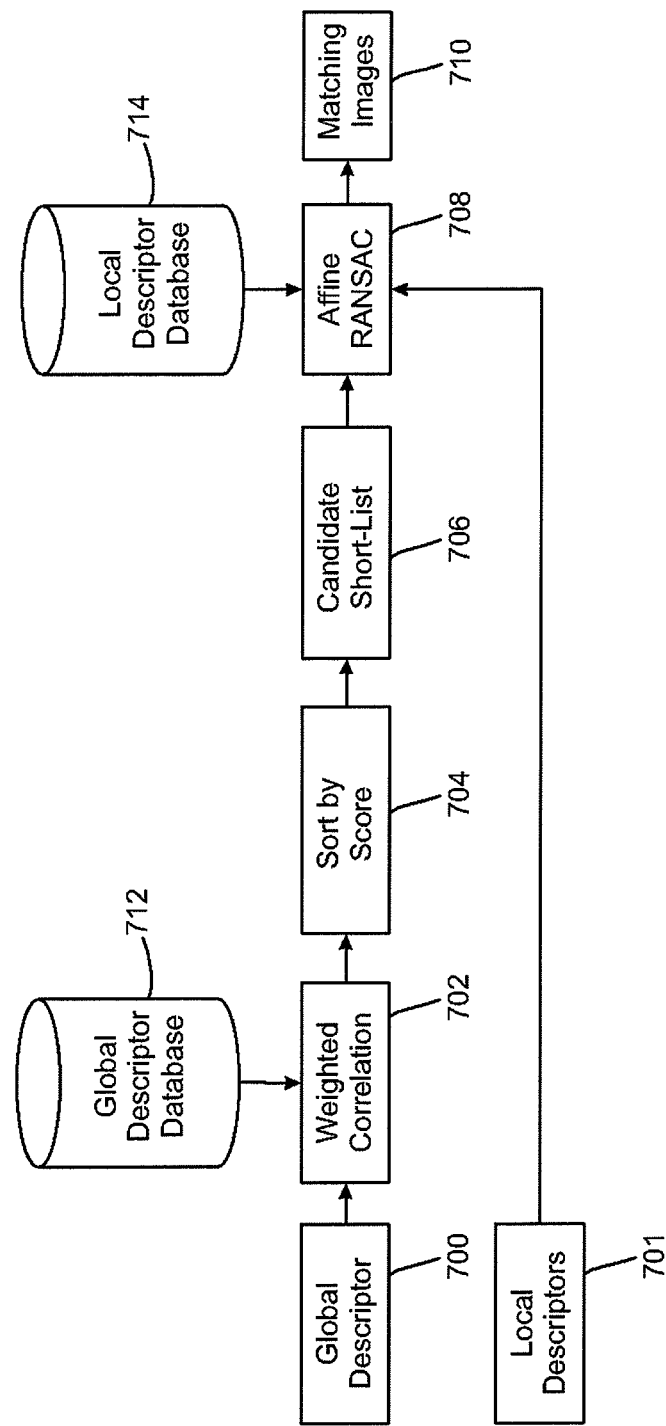
FIG. 17 depicts as a block diagram of an example of a two phase image retrieval.

For database retrieval a two stage approach may be used, as illustrated in FIG. 17. The database images are first ranked by their correlation 702 with the query using the global descriptors 712. Then the pairwise matching 708 is performed, as previously described, on the top images 706 (e.g. top 50 images) in the ranked list of candidates 704. These top images are then re-ranked using the number of pairwise feature matches. Computing a global descriptor correlation score with every database image can be computationally expensive. To speed up this process a partial correlation may first be performed using partial global descriptors. Each global descriptor is composed of N=192 centroid residuals, therefore, using n<N centroids to compute the partial correlation results in an N/n×speed-up. In this example embodiment n=80 for a 2.4× speed-up. Then the top 12,500 images are re-ranked using the full correlation. To boost the MAP performance, the database may be preprocessed to discover similar images. The scores of database images that are related to the top scoring images are then increased. This preprocessing gives about a 2 to 3 percent increase in MAP performance.

The user equipment may comprise a mobile device, a set-top box, or another apparatus capable of processing images such as those described in embodiments of the invention above.

It shall be appreciated that the term user equipment is intended to cover any suitable type of user equipment, such as mobile telephones, portable data processing devices or portable web browsers.

Furthermore elements of a public land mobile network (PLMN) may also comprise video codecs as described above.

In general, the various embodiments of the invention may be implemented in hardware or special purpose circuits, software, logic or any combination thereof. For example, some aspects may be implemented in hardware, while other aspects may be implemented in firmware or software which may be executed by a controller, microprocessor or other computing device, although the invention is not limited thereto. While various aspects of the invention may be illustrated and described as block diagrams, flow charts, or using some other pictorial representation, it is well understood that these blocks, apparatus, systems, techniques or methods described herein may be implemented in, as non-limiting examples, hardware, software, firmware, special purpose circuits or logic, general purpose hardware or controller or other computing devices, or some combination thereof.

The embodiments of this invention may be implemented by computer software executable by a data processor of the mobile device, such as in the processor entity, or by hardware, or by a combination of software and hardware. Further in this regard it should be noted that any blocks of the logic flow as in the Figures may represent program steps, or interconnected logic circuits, blocks and functions, or a combination of program steps and logic circuits, blocks and functions. The software may be stored on such physical media as memory chips, or memory blocks implemented within the processor, magnetic media such as hard disk or floppy disks, and optical media such as for example DVD and the data variants thereof, CD.

The memory may be of any type suitable to the local technical environment and may be implemented using any suitable data storage technology, such as semiconductor-based memory devices, magnetic memory devices and systems, optical memory devices and systems, fixed memory and removable memory. The data processors may be of any type suitable to the local technical environment, and may include one or more of general purpose computers, special purpose computers, microprocessors, digital signal processors (DSPs) and processors based on multi-core processor architecture, as non-limiting examples.

Embodiments of the inventions may be practiced in various components such as integrated circuit modules. The design of integrated circuits is by and large a highly automated process. Complex and powerful software tools are available for converting a logic level design into a semiconductor circuit design ready to be etched and formed on a semiconductor substrate.

Programs, such as those provided by Synopsys, Inc. of Mountain View, Calif. and Cadence Design, of San Jose, Calif. automatically route conductors and locate components on a semiconductor chip using well established rules of design as well as libraries of pre-stored design modules. Once the design for a semiconductor circuit has been completed, the resultant design, in a standardized electronic format (e.g., Opus, GDSII, or the like) may be transmitted to a semiconductor fabrication facility or "fab" for fabrication.

The foregoing description has provided by way of exemplary and non-limiting examples a full and informative description of the exemplary embodiment of this invention. However, various modifications and adaptations may become apparent to those skilled in the relevant arts in view of the foregoing description, when read in conjunction with the accompanying drawings and the appended claims. However, all such and similar modifications of the teachings of this invention will still fall within the scope of this invention.

In the following some examples will be provided.

The invention claimed is:

1. A method comprising:
receiving one or more local descriptors relating to an interest point of an image, wherein the interest point is a corner or an edge that can be searched from the image, and the one or more local descriptors comprises scale or orientation information of the corner or the edge in the image;
compressing the descriptors; and
determining, using a processor, a global descriptor for the image on the basis of the one or more local descriptors.

2. A method according to claim 1 further comprising:
determining a bit rate;
including the compressed global descriptor to a bitstream; and
if there is available bit rate after including the compressed global descriptor, adding one or more compressed local descriptors to the bitstream.

3. A method according to claim 1 further comprising providing the bitstream for searching an image from a database.

4. A method according to claim 1 further comprising defining a base descriptor having gradient bins and spatial bins.

5. A method according to claim 4 further comprising combining two or more of the gradient bins of the base descriptor.

6. A method according to claim 4 further comprising combining two or more of the spatial bins of the base descriptor.

7. A method according to claim 1 further comprising storing gradient information as a distribution; and quantizing the gradient histogram.

8. A method according to claim 1 further comprising reordering location data associated with the descriptors for compressing.

9. A method according to claim 1 further comprising generating a histogram from the locations of the descriptors.

10. A method according to claim 1 further comprising dividing an image into spatial bins; and counting the number of features within each spatial bin.

11. A method according to claim 10 further comprising forming a binary map indicating which spatial bins contains features; and forming a sequence of feature counts representing the number of features in occupied bins.

12. A method according to claim 10 further comprising compressing the sequence of feature counts.

13. An apparatus comprising a processor and a memory including computer program code, the memory and the computer program code configured to, with the processor, cause the apparatus to:
receive one or more local descriptors relating to an interest point of an image, wherein the interest point is a corner or an edge that can be searched from the image, and the one or more local descriptors comprises scale or orientation information of the corner or the edge in the image;
compress the global descriptors; and
determine a global descriptor for the image on the basis of the one or more local descriptors.

14. An apparatus according to claim 13 further comprising computer program code configured to, with the processor, cause the apparatus to:
determine a bit rate;
include the compressed global descriptor to a bitstream; and
if there is available bit rate after including the compressed global descriptor, to add one or more compressed local descriptors to the bitstream.

15. An apparatus according to claim 13 wherein the bitstream is provided for searching an image from a database.

16. An apparatus according to claim 13 further comprising computer program code configured to, with the processor, cause the apparatus to define a base descriptor having gradient bins and spatial bins.

17. An apparatus according to claim 13 further comprising computer program code configured to, with the processor, cause the apparatus to divide an image into spatial bins; and to count the number of features within each spatial bin.

18. An apparatus according to claim 17 further comprising computer program code configured to, with the processor, cause the apparatus to form a binary map indicating which spatial bins contains features; and to form a sequence of feature counts representing the number of features in occupied bins.

19. An apparatus according to claim 13 further comprising computer program code configured to, with the processor, cause the apparatus to combine two or more of the gradient bins of the base descriptor.

20. An apparatus according to claim 13 further comprising computer program code configured to, with the processor, cause the apparatus to combine two or more of the spatial bins of the base descriptor.

21. An apparatus according to claim 13 further comprising computer program code configured to, with the processor, cause the apparatus to store gradient information as a distribution; and quantizing the gradient histogram.

22. An apparatus according to claim 13 further comprising computer program code configured to, with the processor, cause the apparatus to reorder location data associated with the descriptors for compressing.

23. An apparatus according to claim 13 further comprising computer program code configured to, with the processor, cause the apparatus to generate a histogram from the locations of the descriptors.

24. A non-transitory storage medium comprising computer instructions for:
receiving one or more local descriptors relating to an interest point of an image, wherein the interest point is a corner or an edge that can be searched from the image, and the one or more local descriptors comprises scale or orientation information of the corner or the edge in the image;
compressing the descriptors; and
determining a global descriptor for the image on the basis of the one or more local descriptors.

25. A non-transitory storage medium according to claim 24 further comprising computer instructions for:
determining a bit rate;
including the compressed global descriptor to a bitstream; and
if there is available bit rate after including the compressed global descriptor, adding one or more compressed local descriptors to the bitstream.

26. A non-transitory storage medium according to claim 24 wherein the bitstream is provided for searching an image from a database.

27. A non-transitory storage medium according to claim 24 further comprising computer instructions for defining a base descriptor having gradient bins and spatial bins.

28. A non-transitory storage medium according to claim 24 further comprising computer instructions for dividing an image into spatial bins; and counting the number of features within each spatial bin.

29. A non-transitory storage medium according to claim 24 further comprising computer instructions for forming a binary map indicating which spatial bins contains features; and forming a sequence of feature counts representing the number of features in occupied bins.

30. An apparatus comprising:
means for receiving one or more local descriptors relating to an interest point of an image, wherein the interest point is a corner or an edge that can be searched from the image, and the one or more local descriptors comprises scale or orientation information of the corner or the edge in the image;
means for compressing the descriptors; and
means for determining a global descriptor for the image on the basis of the one or more local descriptors.

* * * * *